(12) United States Patent
Jung et al.

(10) Patent No.: US 7,951,839 B2
(45) Date of Patent: May 31, 2011

(54) 6R-(3,6-DIDEOXY-L-ARABINO-HEXOPYRANOSYLOXY)HEPTANOIC ACID, PREPARATION PROCESS FOR THE SAME AND DAUER EFFECT THEREOF

(75) Inventors: Mankil Jung, Seoul (KR); Young Ki Paik, Seoul (KR)

(73) Assignee: KDR Biotech. Co. Ltd., Seoul (KR)

( * ) Notice: Subject to any disclaimer, the term of this patent is extended or adjusted under 35 U.S.C. 154(b) by 725 days.

(21) Appl. No.: 11/927,999

(22) Filed: Oct. 30, 2007

(65) Prior Publication Data

US 2008/0188646 A1  Aug. 7, 2008

Related U.S. Application Data

(62) Division of application No. 10/532,517, filed as application No. PCT/KR2004/002948 on Nov. 15, 2004, now Pat. No. 7,576,225.

(30) Foreign Application Priority Data

Feb. 5, 2004  (KR) .................. 10-2004-0007539

(51) Int. Cl.
*C07D 315/00* (2006.01)
*A61K 31/35* (2006.01)

(52) U.S. Cl. ............ 514/460; 549/420; 549/423
(58) Field of Classification Search ............ 514/460
See application file for complete search history.

(56) References Cited

FOREIGN PATENT DOCUMENTS

KR  10-2004-0042338  5/2004
WO  WO 2004/043944 A1  5/2004

OTHER PUBLICATIONS

James W. Golden and Donald L. Riddle, "A Pheromone Influences Larval Development in the Nematode Caenorhabditis elegans", Science, vol. 218, pp. 578-580, 1982.

*Primary Examiner* — Sreeni Padmanabhan
*Assistant Examiner* — Nathan W Schlientz
(74) *Attorney, Agent, or Firm* — Z. Peter Sawicki; Westman, Champlin & Kelly, P.A.

(57) ABSTRACT

The present invention related to a determination of a stereochemistry, a synthesis and dauer effect of 6R-(3,6-dideoxy-L-arabino-hexopyranosyloxy) heptanoic acid as a pheromone isolated from the *Caenorhabditis elegance* related to suppression of aging and stress. It becomes possible to develop medical substances using the pheromone relating to aging, stress, metabolism, signal transfer system in vivo, and anticancer, obesity and a suppressing agent for aging and stress.

6 Claims, 15 Drawing Sheets

Picture 1 Dauer laver and young adult of C. elegance after treatment of the synthetic pheromone (I)

Picture 2 shows an image illustrating that the C. elegance goes to the dauer larva stage.

Table 3 (Dauer formation effect activity of the pheromone of C. elegance)

6R-(3,6-DIDEOXY-L-ARABINO-EXOPYRANOSYLOXY)HEPTANOIC ACID, PREPARATION PROCESS FOR THE SAME AND DAUER EFFECT THEREOF

This is a divisional of application Ser. No. 10/532,517, filed Apr. 25, 2005, the content of which is hereby incorporated by reference in its entirety.

TECHNICAL FIELD

The present invention relates to an absolute stereo configuration of 6R-(3,6-dideoxy-L-arabino-hexopyranosyloxy) heptanoic acid related to suppress of aging and stress, a preparation process for the same and dauer effect thereof. More particularly, the present invention relates to a determination of a three-dimensional stereochemistry of 6R-(3,6-dideoxy-L-arabino-hexopyranosyloxy)heptanoic acid that is a pheromone first isolated from *Caenorhabditis elegance*, an intermediate required for synthesis of the same, a preparation method and dauer effect of the pheromone.

BACKGROUND ART

Pheromone become known as physiological active substance, are defined as substances that are created in a body of animals and secreted out of the body to act on other individuals of the same species, thereby inducing a specific activation or a variation of physiological phenomena.

According to the previous studies, pheromone secreted from *C. elegance* exists in extremely low concentration, having less than 1,000 Dalton. The pheromone is known as single substance or related compound, which is very stable and non-volatile, having a chromatography property such as short fatty acid hydroxide (Riddle, D. L., Science, 218: 578-580, 1982).

In the thesis of Riddle, although a pheromone moiety is partially purified, an exact chemical configuration and physical properties of pure pheromone are not known yet. In addition, since a pheromone extract from of *C. elegance* used by the researchers is a crude extract partially purified, there is no way to study for finding an exact physiological target and biological mechanisms.

Therefore, the inventors of the present invention mass-cultured *C. elegance* containing the pheromone in the largest state that can induce dauer larva stage due to stress or worsened living environment. And then the inventors isolated and purified the pheromone secreted from the *C. elegance*, and determined the chemical configuration of a purified pheromone. As a result, it has noted that the purified pheromone is 6-(3,5-dihydroxy-6-methyl-tetrahydro-pyran-2-yloxy)heptanoic acid, having a following two-dimensional planar structure formula (Paik et al, Korean Patent Application No. 10-2002-0070591 and PCT application No. PCT/KR03/02059)

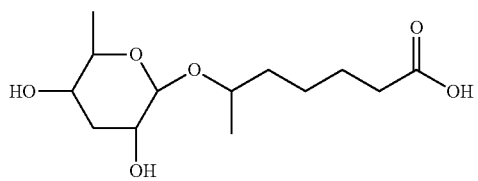

However, a three-dimensional chemical configuration of the above two-dimensional pheromone compound and a total synthesis are not known yet. Since the novel pheromone compound has 5 asymmetric cartons, the stereochemistry configuration of the pheromone compound may be possibly provided with 36 stereoisomers. Therefore, a stereochemistry configuration should be essentially determined to synthesize the pheromone compound identical with exact natural pheromone having a correct stereochemistry.

In addition, in order to research aging, stress, metabolism, signal transfer system in vivo, to develop medical substances relating to anticancer, obesity and a suppressing agent for aging and stress, and to research active target protein body of the pheromone, it is inevitably required to develop full synthesis method for mass-production of the pheromone.

Therefore, the inventors determined a three-dimensional stereochemistry configuration of the pheromone isolated from *C. elegance* to synthesize the pheromone identical with natural pheromone using spectroscopic technologies. In addition, the inventors successfully performed stereospecific total synthesis, thereby obtaining the pheromone fully identical with the natural pheromone. This method provides the mass-production of the pheromone, overcoming the limited amount of natural pheromone. In addition, it is identified that the pheromone obtained according to the present invention has Bauer formation effect in vivo test using *C. elegance*.

DISCLOSURE OF INVENTION

Technical Solution

Therefore, it is an object of the present invention to provide a pheromone compound having a stereochemistry formula (I-I).

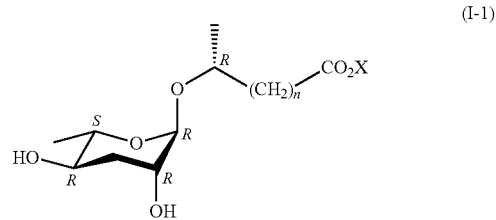

(I-1)

where, X is hydrogen, alkali or alkali earth metal and n is 1-6 integer.

It is another object of the present invention to provide a method for mass-production of the pheromone with high yield.

It is still another object of the present invention to determine a three-dimensional stereochemistry configuration to accurately synthesize the pheromone.

It is still yet another object of the present invention to provide an intermediate for mass-production of the pheromone with high yield.

It is still yet another object of the present invention to provide a use of a pheromone as medical agent for curing disease relating to aging and stress.

MODE FOR INVENTION

A three-dimensional stereochemistry formula (1) of 6R-(3,6-dideoxy-L-arabinohexopyranosyloxy)heptanoic acid as a pheromone compound isolated from *C. elegance* is determined according to spectroscopic analysis such as HR-MASS, IR, DEPT, 2D-NMR (HMBC, HMQC, NOE, ROESY, and TOCSY).

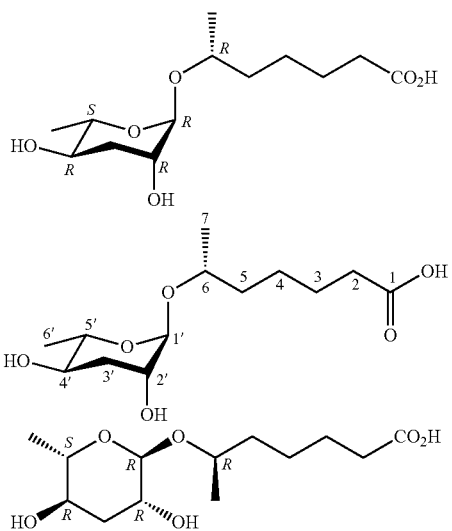

Figure 1:
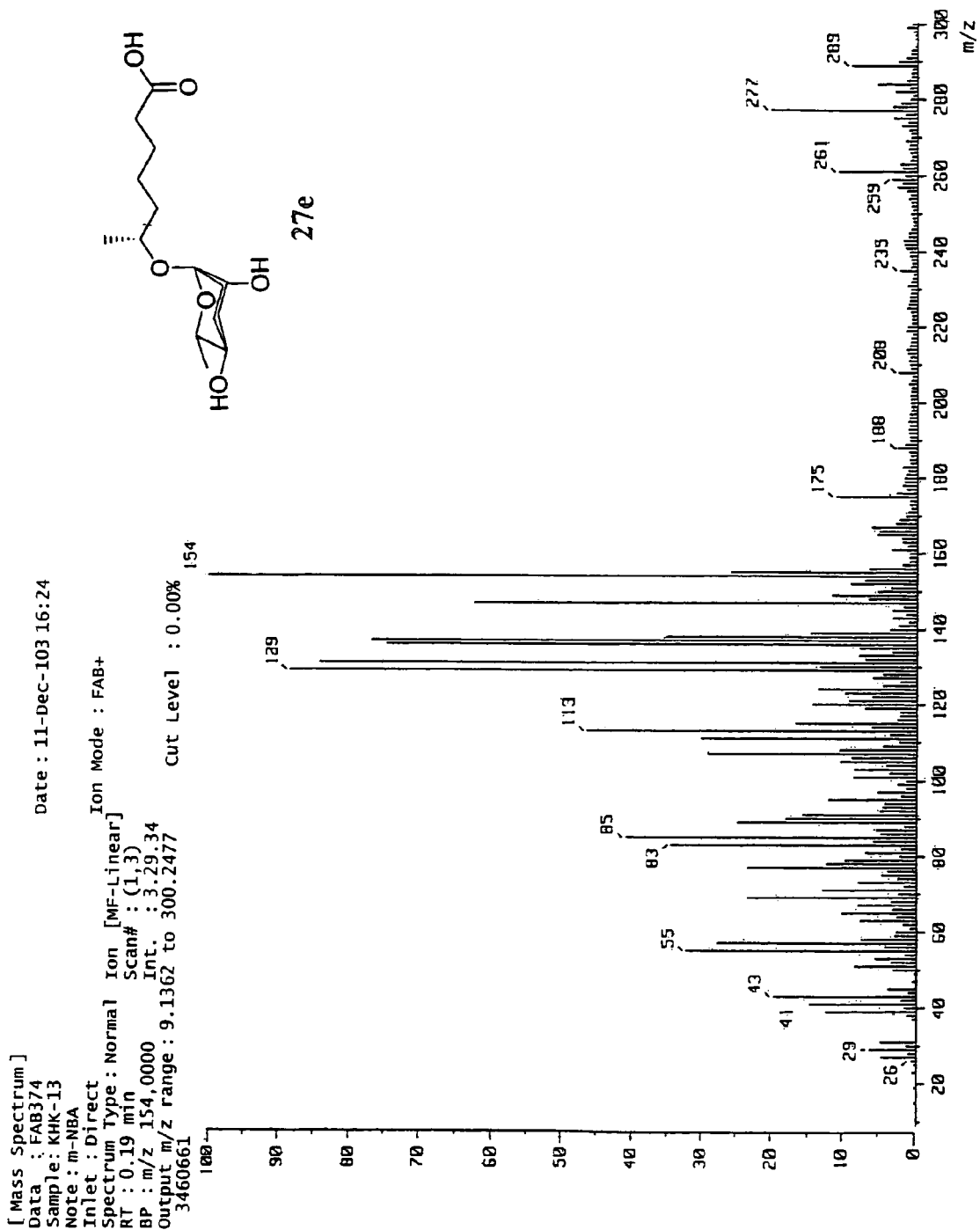
FIG. 1 is a HR-MS-FMB spectrum of a pheromone of stereochemistry formula (1) according to the present invention.
Figure 2:
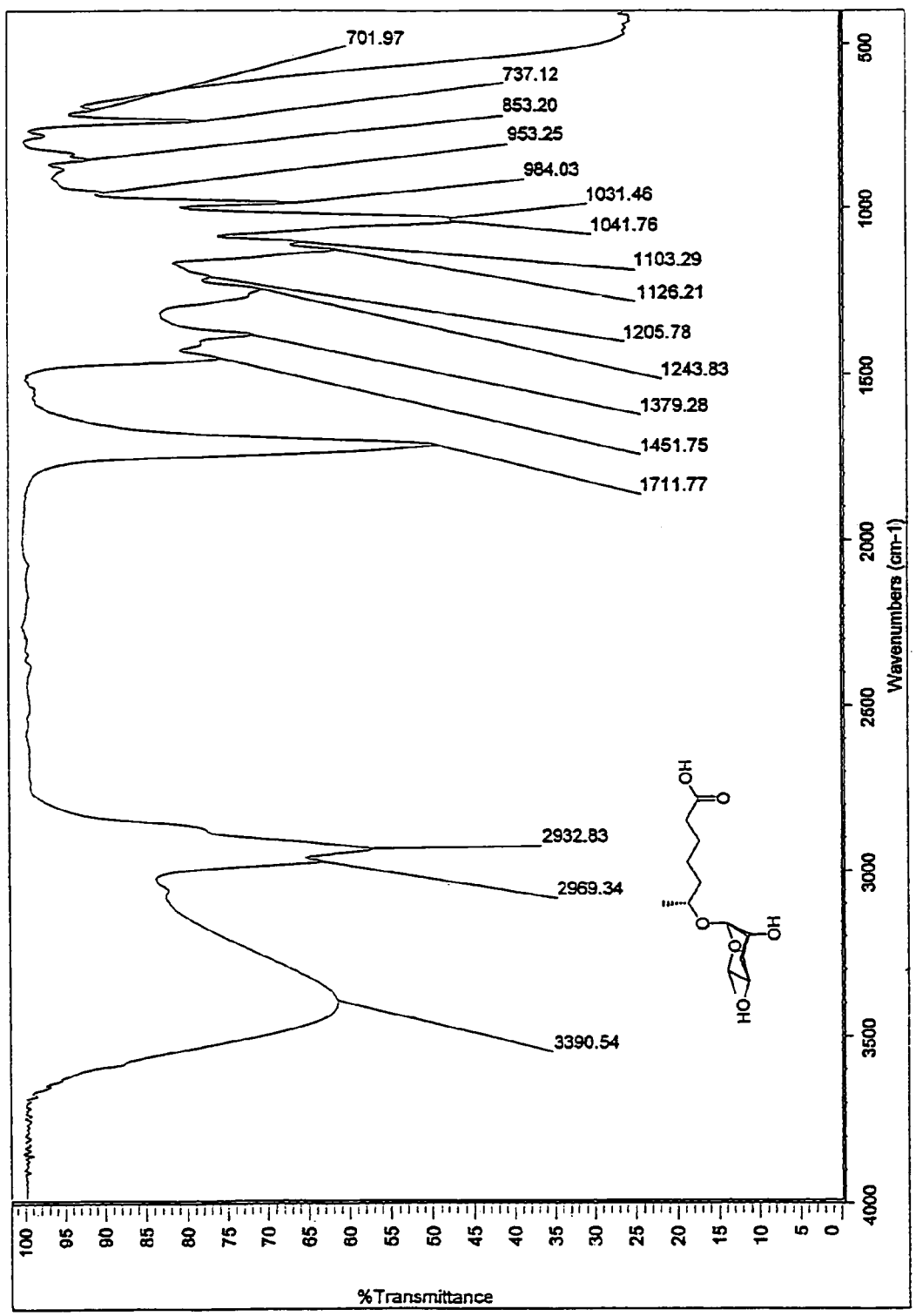
FIG. 2 is an IR spectrum of the pheromone according to the present invention.

A pure molecular weight of the pheromone, 6R-(3,6-dideoxy-L-arabino-hexopyranosyloxy)heptanoic acid, is 276 dalton, and a monocular formula of the pheromone is $C_{13}H_{24}O_6$. A calculated high-resolution mass number of the pheromone is 276.1651. It is noted that a high-resolution mass number measured by a high resolution-FAB is 276.1652, and this mass number is almost identical to the calculated mass number (see FIG. 1). Functional groups of relative carbonyl and hydroxy groups of the pheromone molecule are identified by an infrared (IR) analysis (see FIG. 2).

In order to determine the three-dimensional stereochemistry configuration of the novel pheromone compound of formula (I), 2D-proton.nuclear magnetic resonance spectrum ($^1$H-NMR) is measured by using dutro-methanol (CD$_3$OD) as a solvent. A C-13 nuclear magnetic resonance spectrum ($^{13}$C-NMR) is also measured by using dutro-methanol (CD$_3$OD) as a solvent. The chemical shift is represented by ppm.

Figure 3:
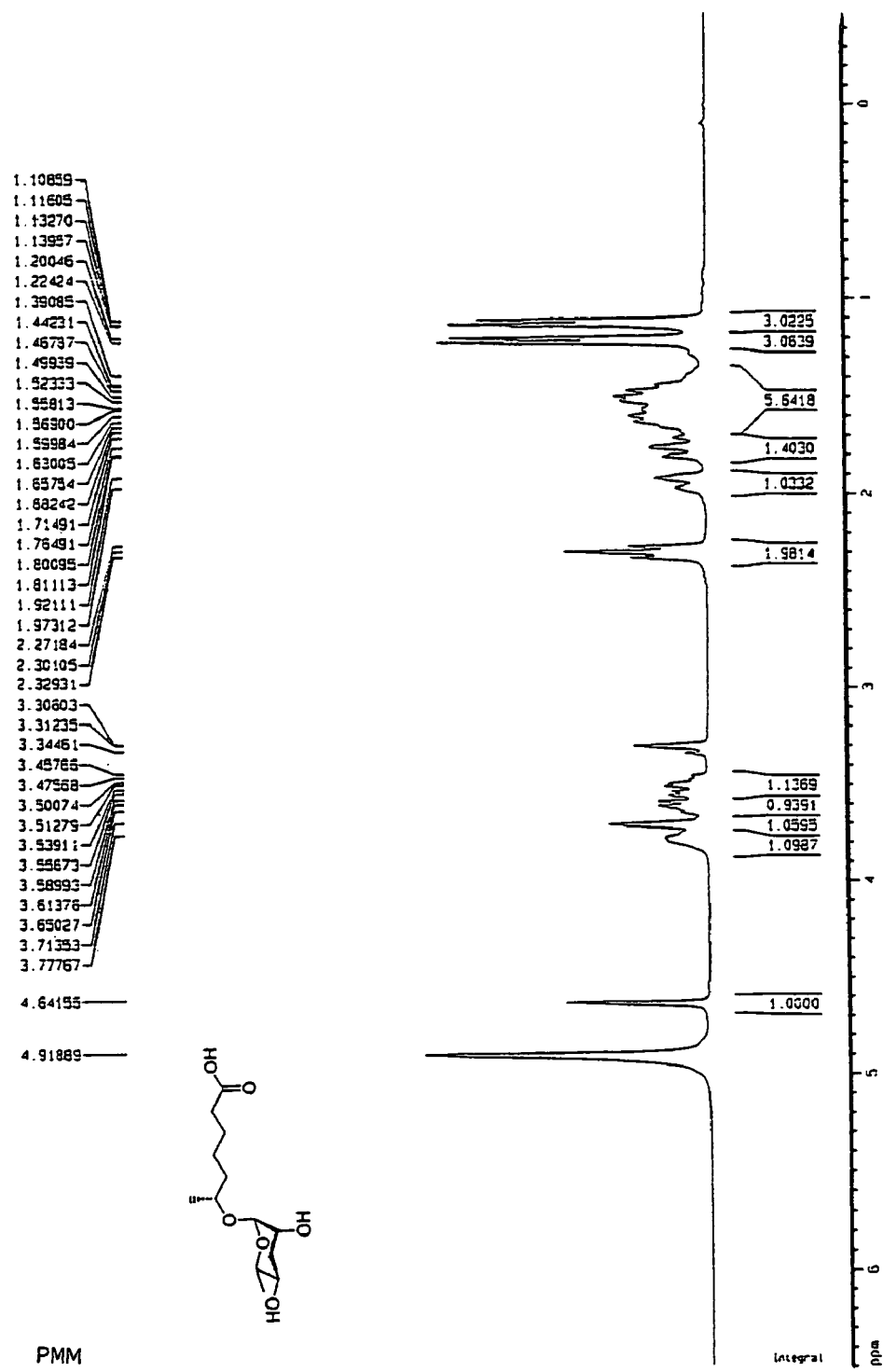
FIG. 3 is a $^1$H-NMR spectrum of the pheromone according to the present invention.
Figure 4:
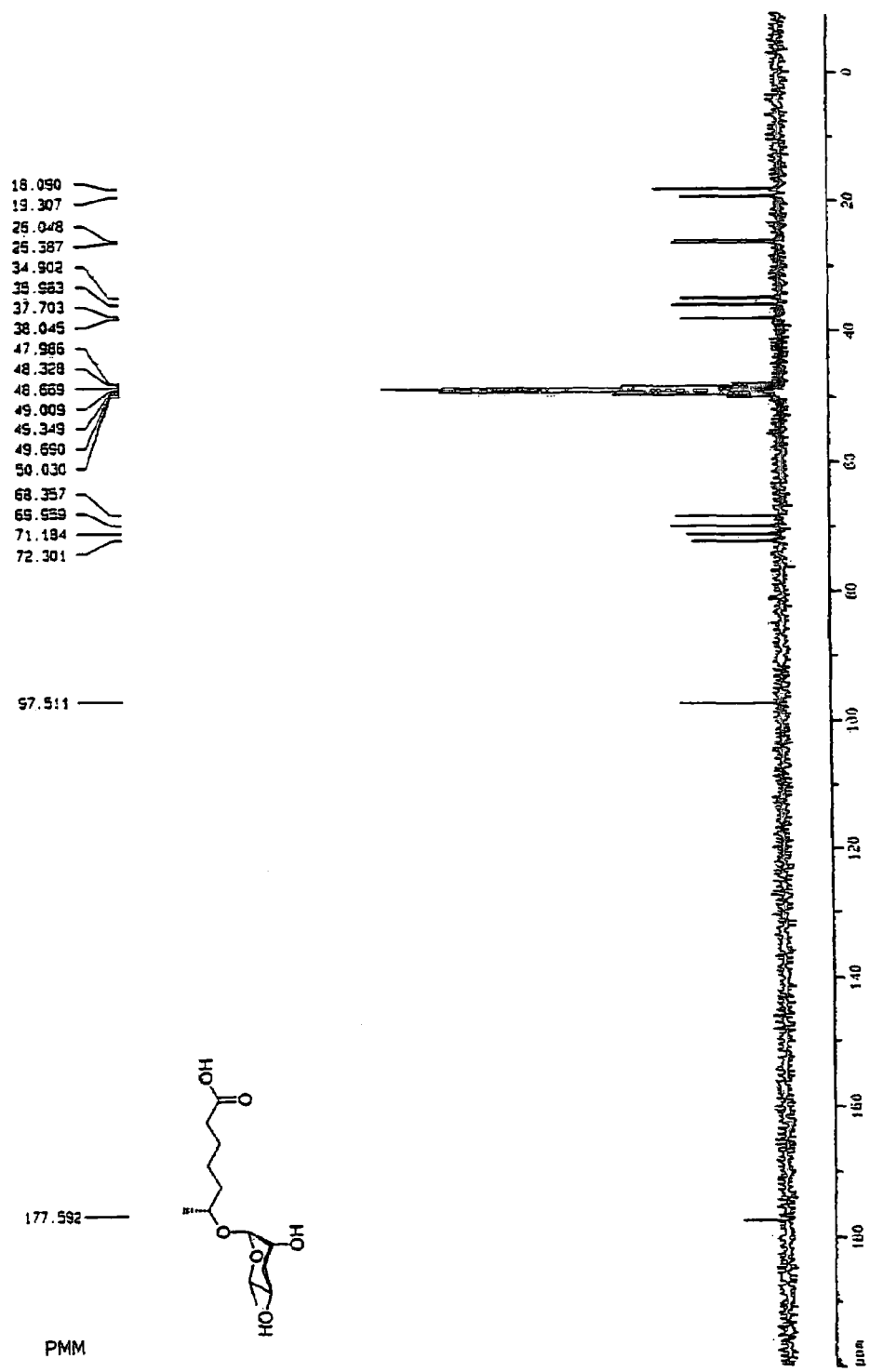
FIG. 4 is a $^{13}$C-NMR spectrum of the pheromone according to the present invention.
Figure 5:
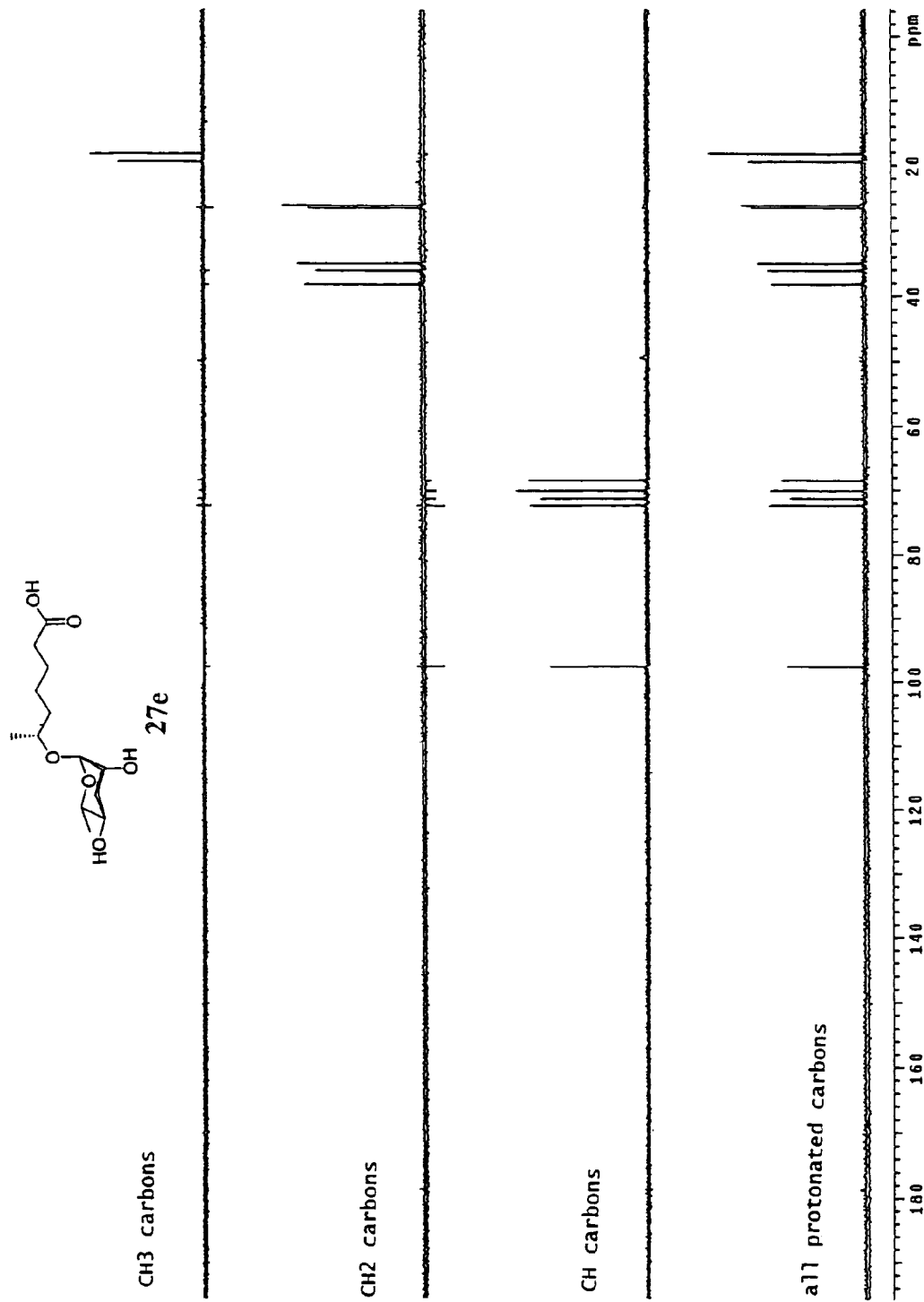
FIG. 5 is a $^{13}$C-NMR DEPT spectrum of the pheromone according to the present invention.
Figure 6:
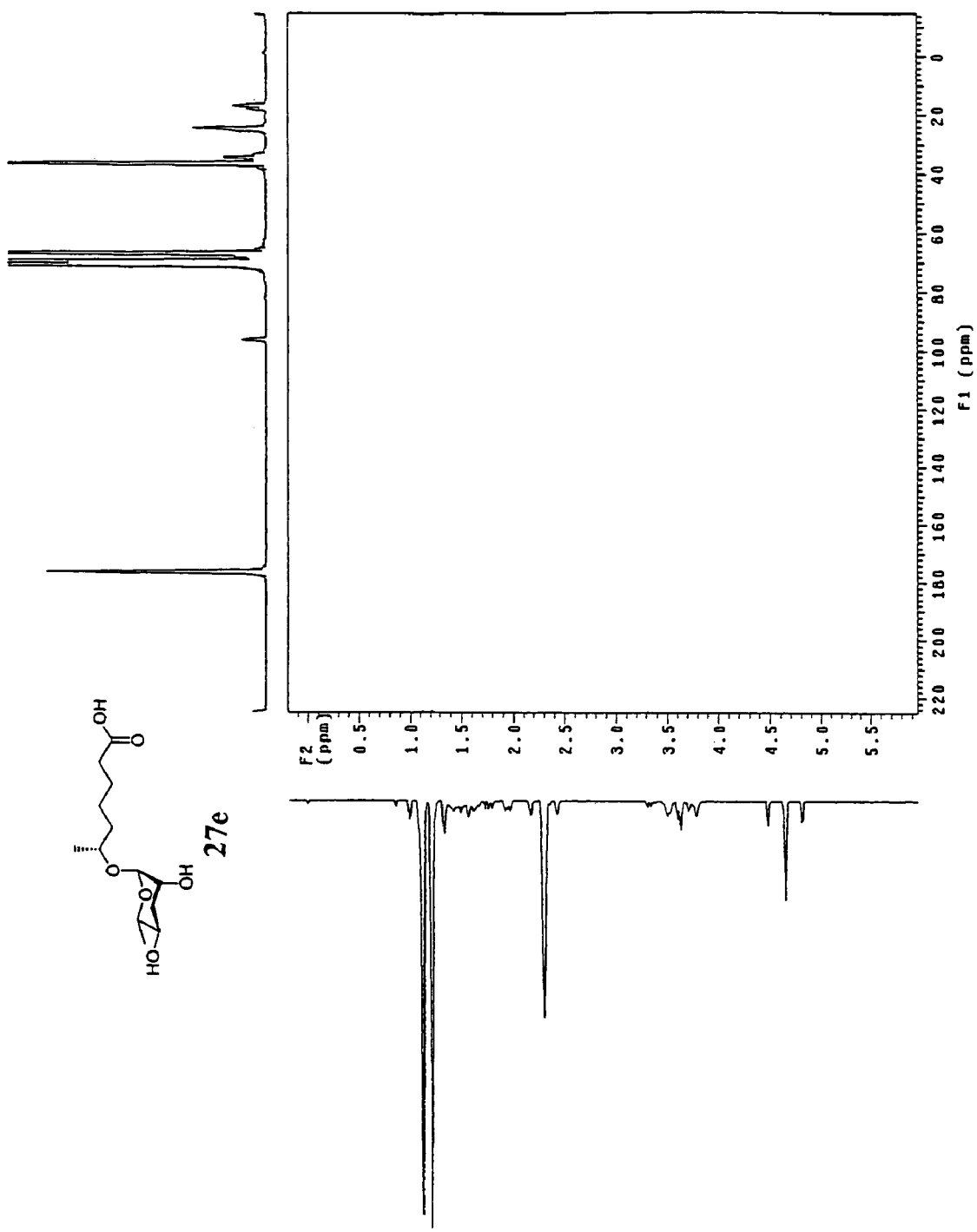
FIG. 6 is a 2D-NMR HMBC spectrum of the pheromone according to the present invention.
Figure 7:
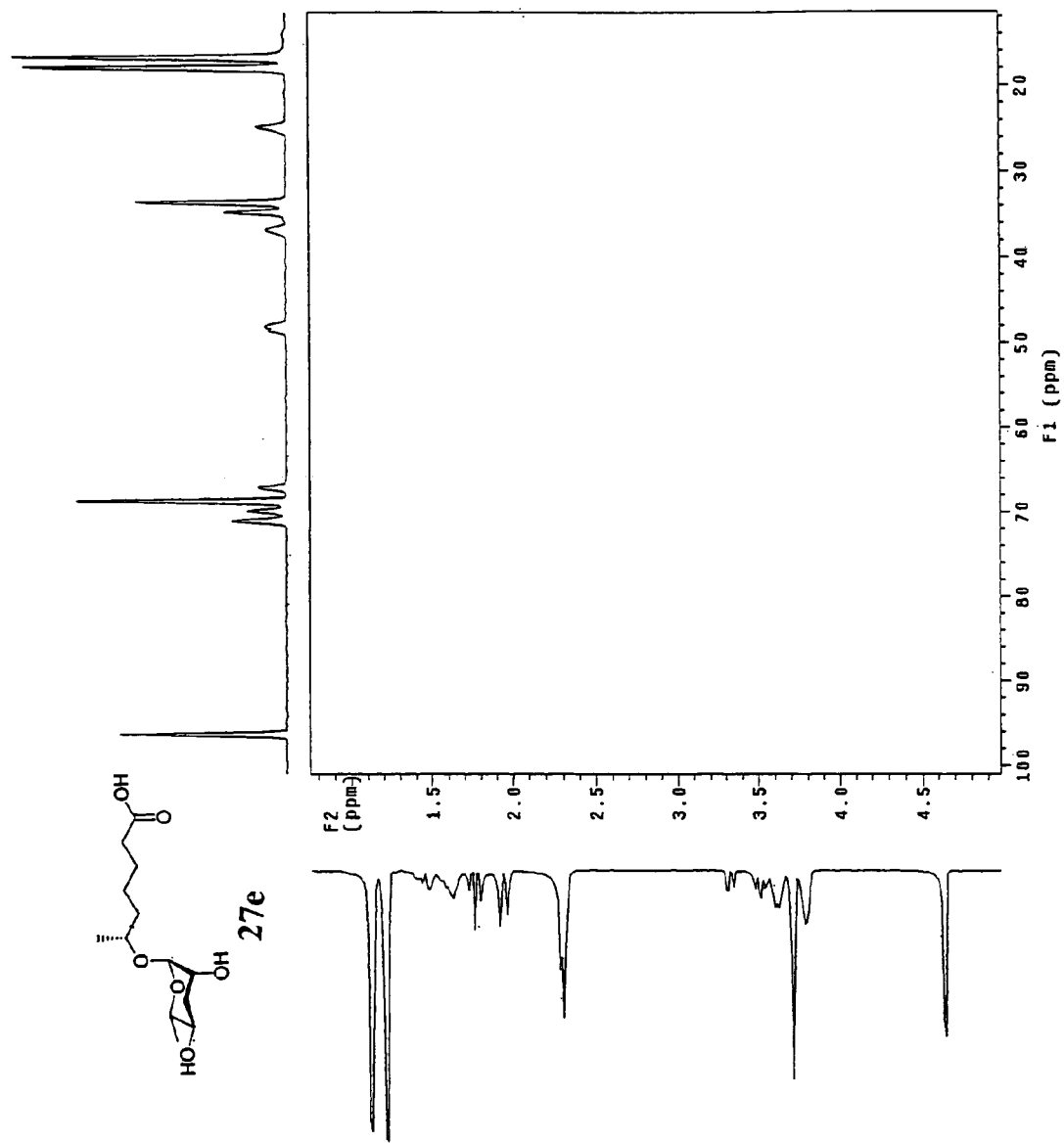
FIG. 7 is a 2D-NMR HMQC spectrum of the pheromone according to the present invention.
Figure 8:
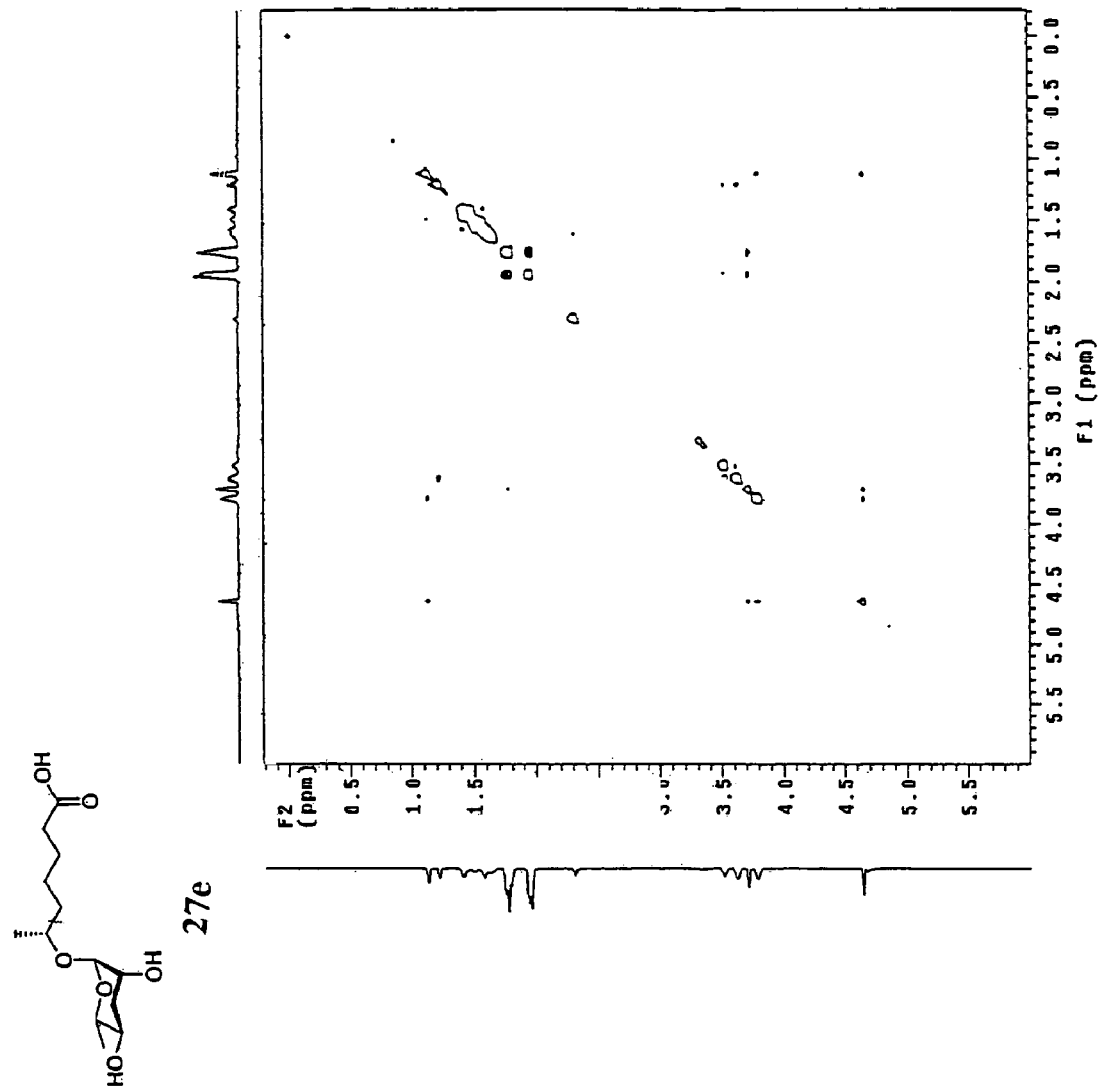
FIG. 8 is a 2D-NMR ROESY spectrum of the pheromone according to the present invention.
Figure 9:
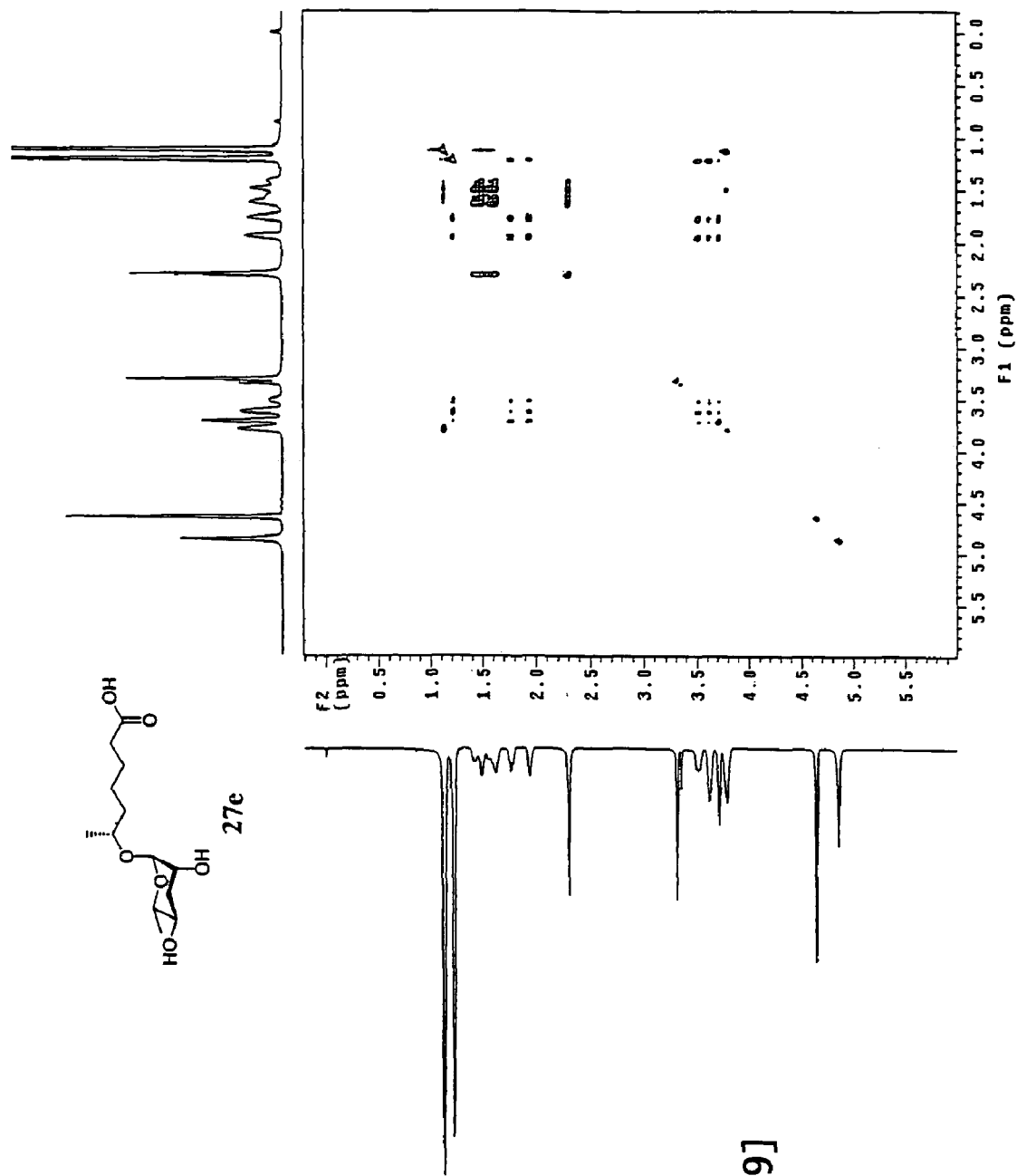
FIG. 9 is a 2D-NMR TOCSY spectrum of the pheromone according to the present invention.

After the location of each carbon is identified by $^1$H-NMR (see FIG. 3), $^{13}$C-NMR (see FIG. 4) and DEPT (see FIG. 5), the chemical shift of $^1$H— and $^{13}$C— is measured by using HMBC (see FIG. 6), HMQC (see FIG. 7), ROESY (see FIG. 8), and TOCSY (see FIG. 9) spectrums to identify the accurate relation of the $^1$H— and $^{13}$C. Table 4 shows a result of HMBC spectrum.

Figure 10:
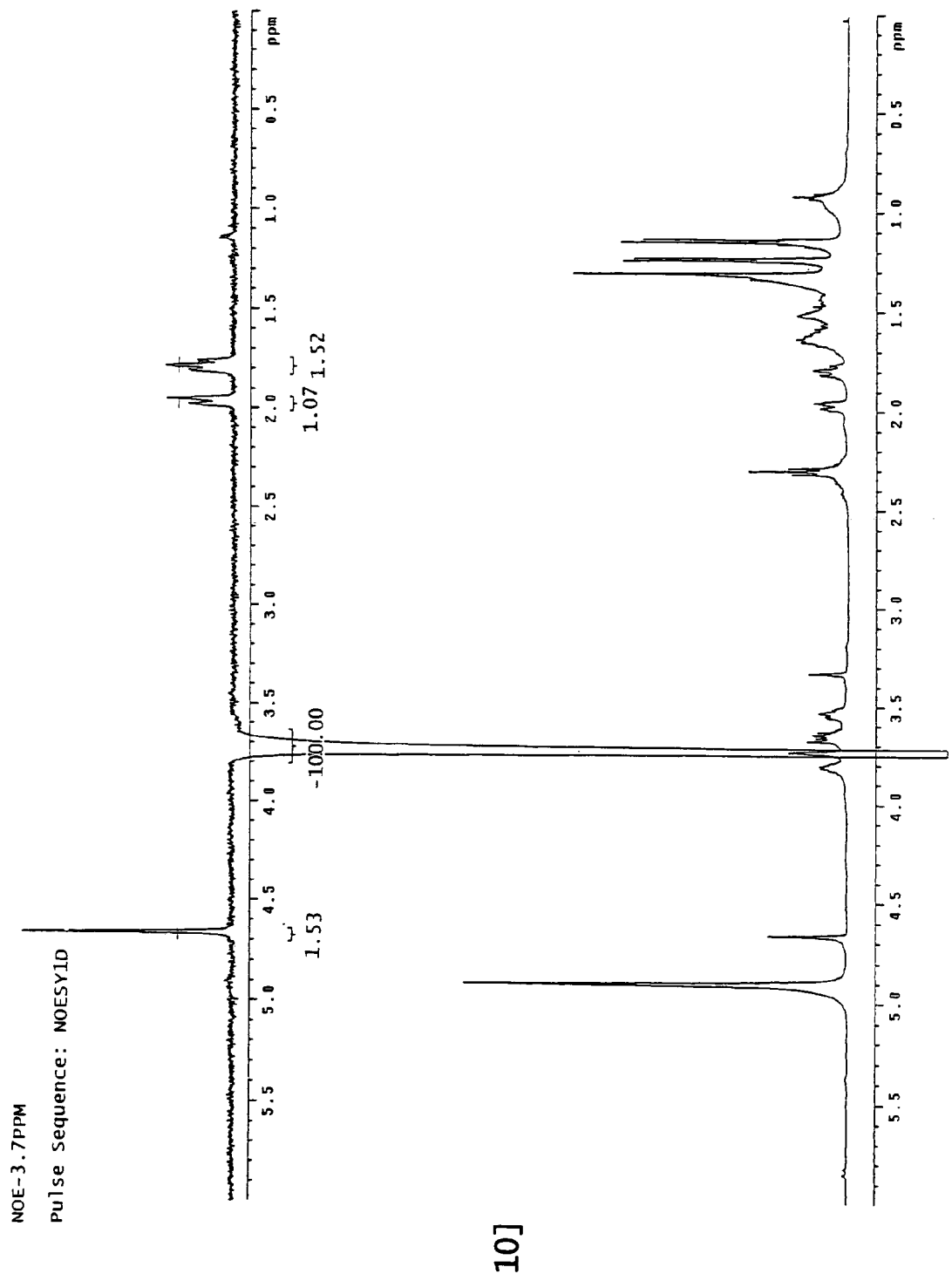
FIG. 10 is a 2D-NMR NOE(1) spectrum of the pheromone according to the present invention.
Figure 11:
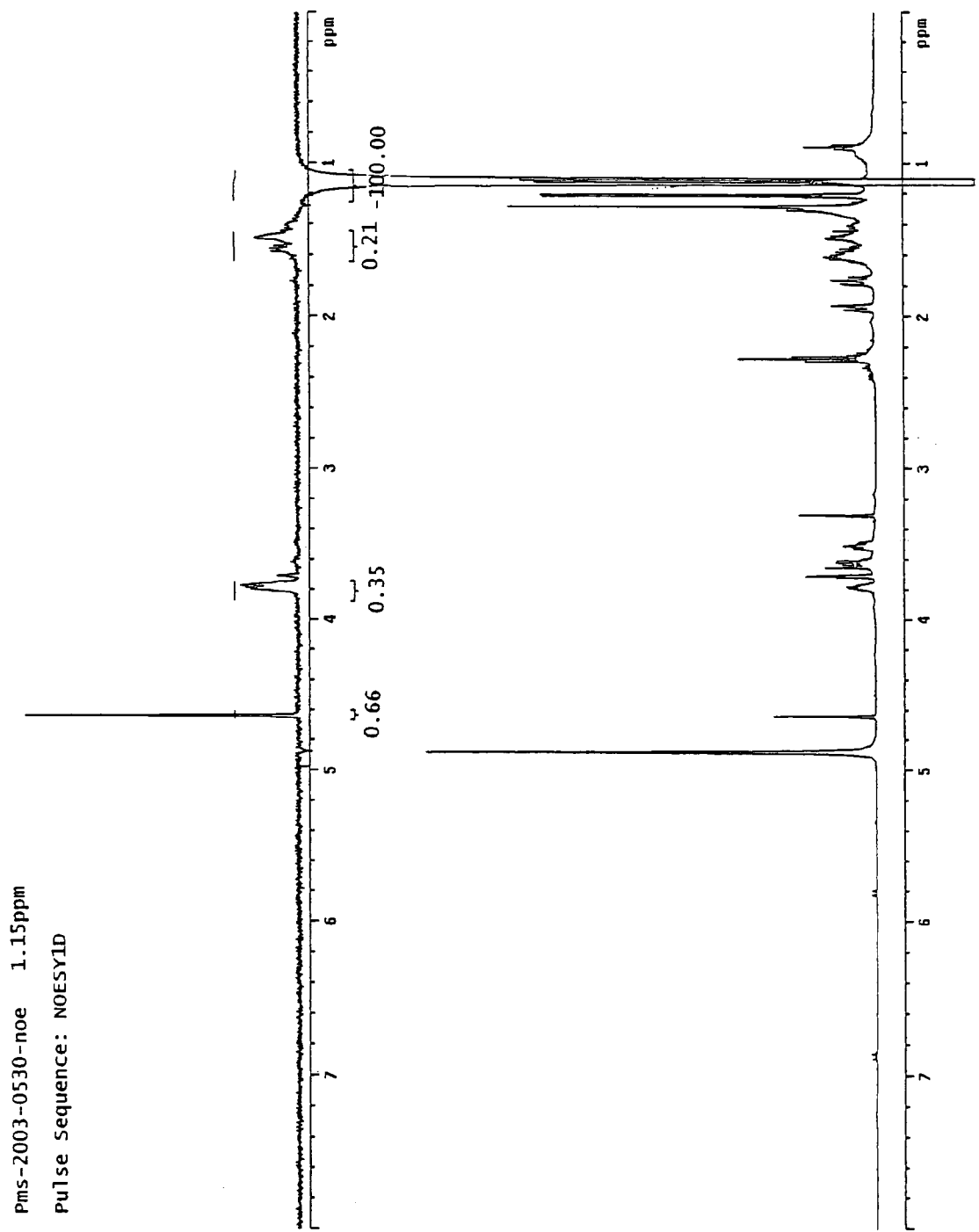
FIG. 11 is a 2D-NMR NOE(2) spectrum of the pheromone according to the present invention.
Figure 12:
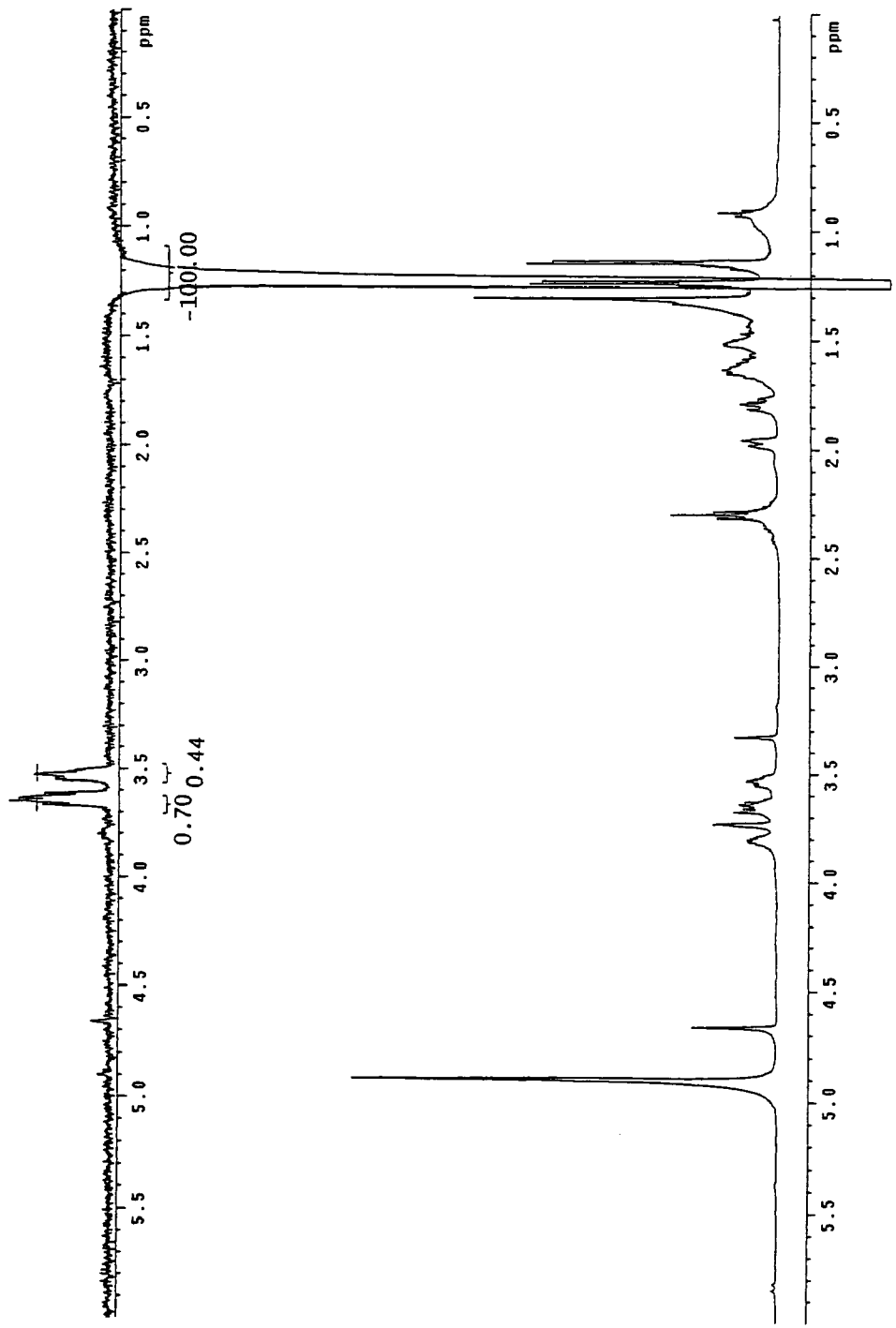
FIG. 12 is a 2D-NMR NOE(3) spectrum of the pheromone according to the present invention.
Figure 13:
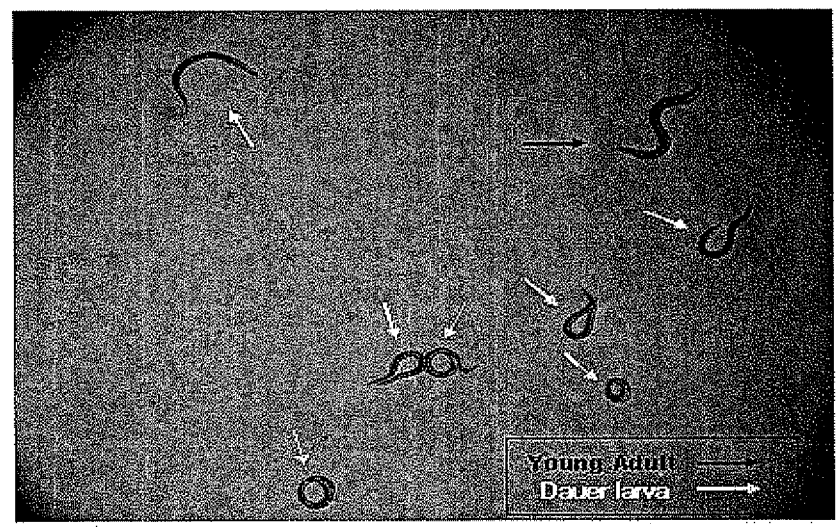
FIG. 13 is a picture of a Dauer laver and young adult of C. elegance after treatment of the synthetic pheromone (I).
Figure 14:
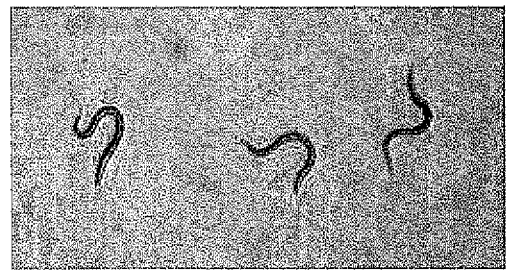
FIG. 14 is a picture showing an image illustrating that the C. elegance goes to the dauer larva stage.
Figure 15:
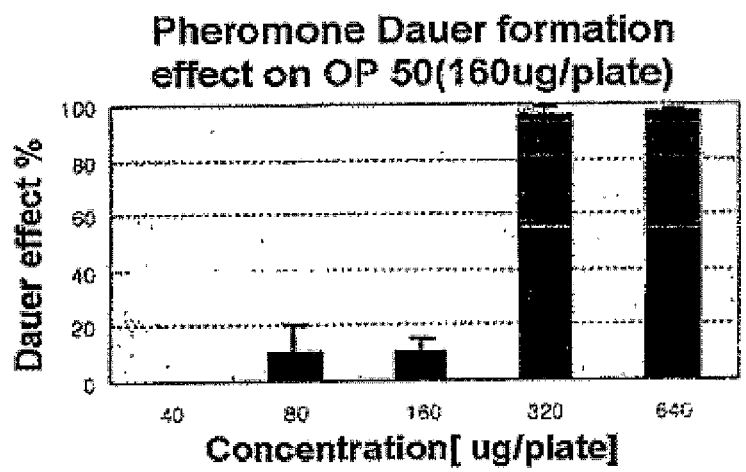
FIG. 15 Table 3, is a table showing Dauer formation effect activity of the pheromone C. elegance.

In order to measure the stereo interrelation in the three-dimensional space, the two-dimensional NMR technology of NOE is used. FIGS. 10 through 12 show the obtained NOE spectrum.

The 6R-(3,6-dideoxy-L-arabino-hexopyranosyloxy)heptanoic acid of the stereochemistry formula (I) is obtained by a coupling reaction of reactants represented in formulas (II) and (III).

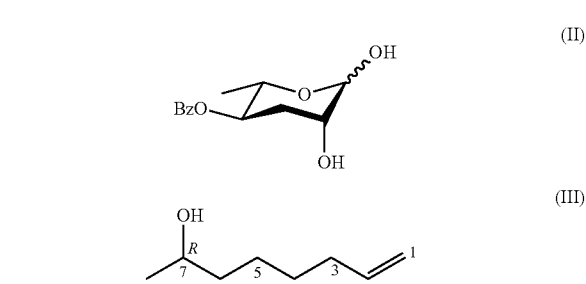

2,4-di-O-benzoyl-3,6-dideoxy-L-arabino-hexopyranose of formula (II) is synthesized as shown in the following reaction formula 1 from L-rhamnose monohydrate of formula (IV).

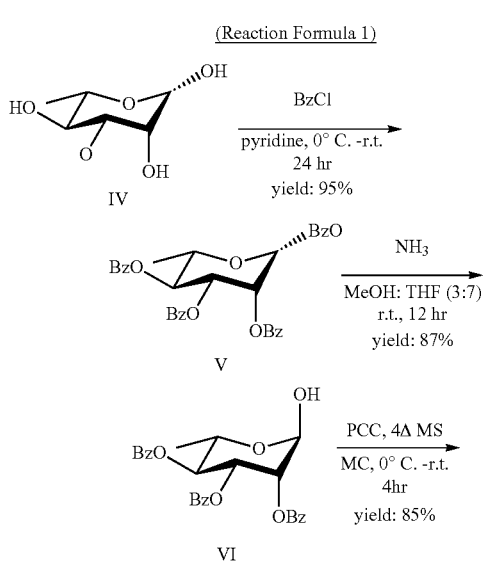

-continued

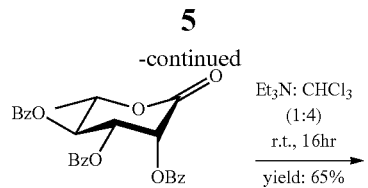
VII

Et₃N: CHCl₃
(1:4)
r.t., 16hr
yield: 65%

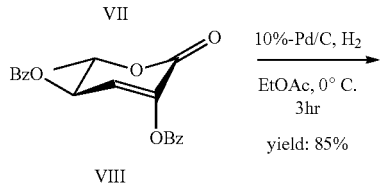
VIII

10%-Pd/C, H₂
EtOAc, 0° C.
3hr
yield: 85%

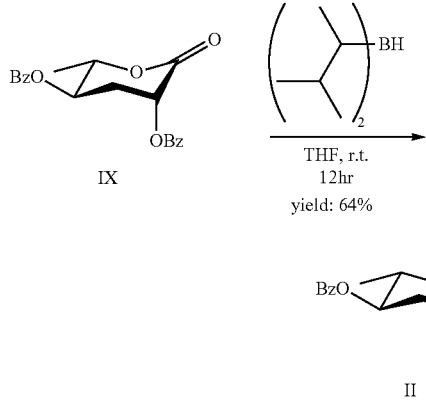
IX

THF, r.t.
12hr
yield: 64%

II where, Bz is benzoyl or benzyl group.

Compound of formula (V) is produced from the compound of formula (IV) by protecting 4 hydroxide groups of the compound (IV) using benzoylchloride. Compound (VI) is produced by selectively eliminating C-1 benzoyl group of the compound (V) using ammonia.

Ketone compound of formula (VII) is produced by oxidizing the C-1 hydroxide group of the compound (VI) using pyridinum chlorchlomate (PCC). Compound of formula (VIII) is produced by selectively eliminating C-3 benzoyl group of the compound of formula (VII). Compound of formula (IX) is obtained from the compound of formula (VIII) through hydrogenation in the presence of 10% palladium/carbon catalyst. At this point, the C-2 O-benzoyl group of the compound of formula (IX) has a β-direction.

Finally, by reducing C-1 ketone group of the compound of formula (IX) using chiral diisoamylborohydride, α-anomer of 2,4-di-O-benzoyl-3,6-dideoxy-L-arabinohexopyranose (II) is produced as a stereospecific C-1 intermediate.

Another reactant, the compound of formula (III) is produced according to following reaction formula 2 from (R)-(+)-1,2-epoxypropane as a raw material.

(Reaction Formula 2)

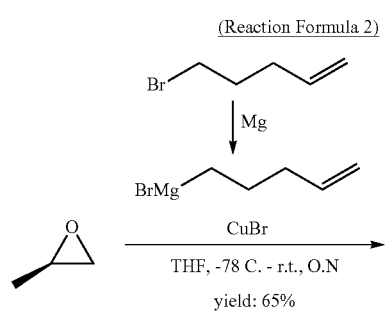

CuBr
THF, -78 C. - r.t., O.N
yield: 65%

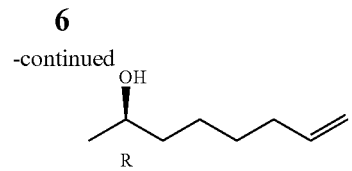

As shown in the reaction formula 2, the (R)-(+)-1,2-epoxypropane is added to separately synthesized 1M 4-pentenyl magnesium bromide, obtaining a (2R)-7-octen-2-ol (III).

The compound of formula (I) is obtained by reacting the compounds of formulas (II) and (III) through following reaction formula 3.

(Reaction Formula 3)

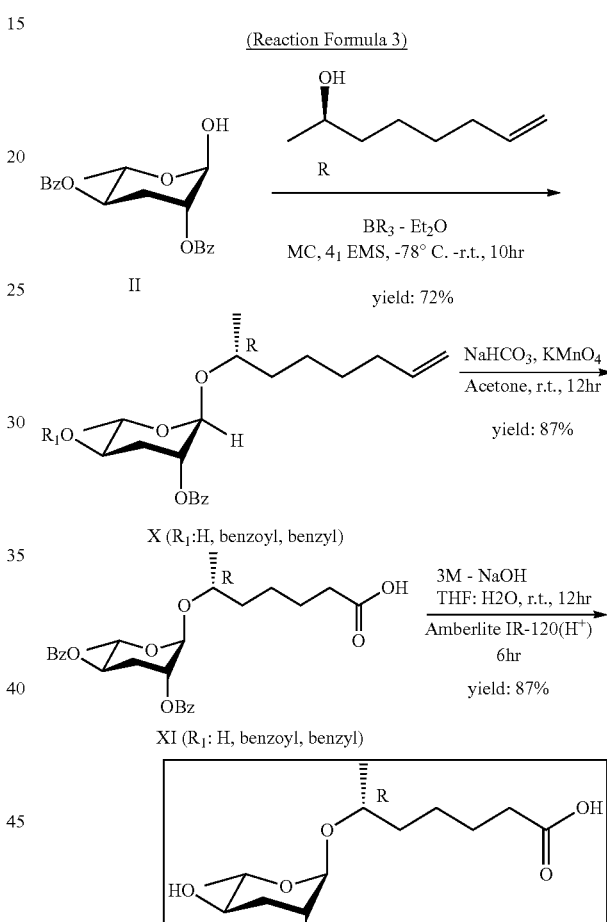

Coupling compound, (2R)-oct-7-en-2-yl-2,4-di-O-benzyl-3,6-dideoxy-α-L-arabino-hexopyranoside (X) is obtained through acetalation of the compounds of the formulas (II) and (III) on the presence of Lewis acid catalyst. (6R)-6-(2,4-di-Obenzyl-3,6-dideoxy-α-L-arabino-hexopyranosyl)heptanoic acid (XI) as an organic acid is produced through a single reaction of terminal aliphatic double bond of the compound of formula (X) using potassium permanganate as an oxidant. Finally, the compound of formula (I) is produced by eliminating C-2 and C-4 benzoyl groups of the compound of formula (XI) by sodium hydroxide and acidifying using amberlite resin type acid such as amberlite and amberlite IR-120.

In addition, the compound of formula (I) reacts with a base to form addition salts of the compound of formula (I-1). As the rose, alkali or alkali earth metal salt that can be pharmaceutically allowed may be used.

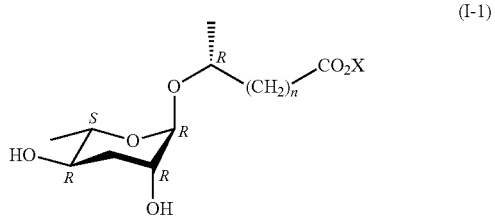

(I-1)

where, X is hydrogen, alkali or alkali earth metal and n is 1-6 integer.

It is noted through the spectrometry (2D-NMR, C-13 NMR, IR, HRMS, specific rotation=$[\alpha]D^{20}$=−81.0 (c=0.1, MeOH)) that the spectrum of the fully synthetic compound of formula (I) is identical to that of the natural pheromone.

Since the total synthesis starts with L-rhamnose, an absolute stereo configuration of which is well known, and a measured value of all spectrum of the compound of formula (I) is identical to that of the natural pheromone, it can be noted that the absolute stereoconfiguration of the natural pheromone isolated from the C. elegance is the formula (I).

In addition, in the course of the reaction formula 3 synthesis, a variety of derivatives of the formula (I-1) is prepared by coupling other alkyl organic acid having a 1-6 carbon chain, instead of the formula (III).

In addition, in the course of the reaction formula 3 synthesis, when a 7S-stereoisomer of the formula (III) is reacted, 6S stereoisomer (I-2) of the compound (I) can be synthesized.

In the course of preparing the compound of formula (II) from the compound of formula (IX) in the reaction formula 1, when C-1' β-epimer of the compound of formula (II) obtained is used, compound of formula (I-3) having C-1' S stereoisomer can be synthesized.

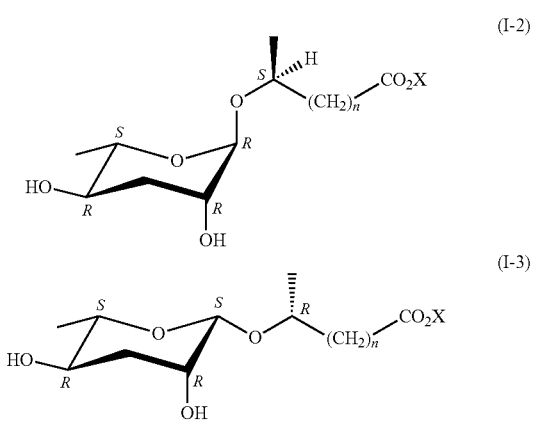

where, n is 1-6 integer and X is H, alkali or alkali earth metal.

By the above synthesis, the inventive pheromone (I) and the derivatives thereof can be mass-produced. Therefore, it becomes possible to research active target protein body of the pheromone and medical efficacy relating to suppress of aging and stress.

Next, dauer formation effect of the compound of 6R-(3,6-dideoxy-L-arabino-hexopyranosyloxy)heptanoic acid (I), which is synthesized according to the present process of the invention, is measured using C. elegance.

That is, the dauer formation effect of the synthetic pheromone is measured using C. elegance under different feed, temperature and crowd density conditions from each other.

Although it should be passed from an L2 first half step or L3 second half step to an adult step in a condition where the feed and temperature (15-25° C.) are proper and the crowd density is low, when the synthetic pheromone is mixed, the step goes to clatter larva stage.

The C. elegance in the dauer larva does not eat and move, being fanned in a circular-shape. For comparison, seven C. elegances in the dauer larva and one C. elegance in the adult step are comparatively observed. As a result, it is noted that the synthetic pheromone greatly affects the dauer formation effect. In Picture 1, it can be noted that the C. elegance is not grown without moving.

Picture 2 C. elegance in the Dauer Laver

Next, as shown in Table 3, it can be noted that 100% of the dauer formation effect can be obtained when 320 μg/plate of the synthetic pheromone and is used.

Such a result becomes the base for research to be advanced and much amount of the pheromone is required for a variety of searches. Therefore, this shows that the synthetic pheromone is important. That is, since the synthesis of a large amount of pheromone and a variety of derivatives becomes possible according to the present invention, the more preferable research may be expected.

DETAILED DESCRIPTION OF THE INVENTION

The present invention will now be described more apparent by describing in detail exemplary embodiments thereof.

Embodiment 1

Synthesis of
1,2,3,4-tetra-O-benzol-L-rhamnopyranose (V)

L-rhamnose monohydrate (IV) (7.5 g, 41.2 mmol) is dissolved in dry pyridine (100 ml), and then benzoylchloride (28.7 ml, 0.247 mmol) is added thereto in a state where the temperature is lowered to 0° C. The temperature of the reactant is gradually increased to room temperature, and water (15 ml) is added after 16 hours, completing the reaction.

An obtained product is extracted with $CH_2Cl_2$ (50 ml×2). It is washed by 1M HCl (40 ml×2) and saturation $NaHCO_3$ solution (40 ml) and dried by MgSO. The solution is vacuum concentrated, and then the compound (V) (22.7 g, 95%, α:β=2:1) is isolated using flash column chromatography (toluene/EtOAc, 10:1, v/v).

V α; an amorphous white solid, Rf=0.58 (toluene/EtOAc, 10:1, v/v);

$[\alpha]D^{22}$=+82.0 (c=1.5, $CHCl_3$) [lit. 41 $[\alpha]D$=+80.0 (c=1.5, $CHCl_3$)];

IR(film)Vmax 3066, 3032, 2986, 1730, 1601, 1452, 1260, 1176, 1094, 1068, 1027, 965 $cm^{-1}$;

$^1$H NMR (250 MHz, $CDCl_3$) δ 8.22-7.25 (m, 20H, aromatic H), 6.57 (d, 1H, J=1.6 Hz H-1), 6.01 (dd, 1H, J=3.4, 10.2 Hz H-3), 5.89 (dd. 1H, J=1.9, 3.2 Hz H-2), 5.82 (t, 1H, J=10.0 Hz H-4), 4.41-4.35 (m, 1H, H-5), 1.42 (d, 3H, J=6.2 Hz —$CH_3$);

$^{13}$C NMR (62.9 MHz $CDCl_3$) δ 165.8 (2), 165.4, 164.1, 134.0, 133.8, 133.6, 133.4, 130.2 (2), 130.1 (2), 129.8 (4), 129.1 (2), 129.0 (2), 128.8 (2), 128.7 (2), 128.6 (2), 128.4 (2), 91.4 (C-1, α), 71.3, 70.0, 69.8, 69.4, 17.8 (C-6);

An HRMS (FAB) calculated value for $C_{34}H_{28}NaO_9$ ($M^+$+Na) m/z is 603.1631, an actual measured value is 603.1637

Embodiment 2

Synthesis of 2,3,4-tri-O-benzoyl-L-rhamnopyranose (VI)

The compound (V) (22.4 g, 38.6 mmol) is dissolved in MeOH:THF (3:7, 400 ml, and then $NH_3$ gas is bubbled for 15 minutes at 0° C. and stirred at 0° C. for 1 hour. The reaction process is identified by thin layer chromatography while repeating the above process. The solvent is vacuum concentrated, and then the compound (VI) (16 g, 87%, α:β=14:1) is isolated using flash column chromatography (toluene/EtOAc, 10:1, v/v).

VI α; a white solid, Rf=0.18 (toluene/EtOAe, 10:1, v/v);

$[α]D^{23}$=+236.0 (c=1.0, $CHCl_3$);

IR(film) Vmax 3458, 3062, 2985, 2935, 1727, 1601, 1451, 1348, 1264, 1102, 1069, 1027 $cm^{-1}$;

$^1$H NMR (250 MHz $CDCl_3$) δ 8.12-7.22 (m, I5H, aromatic H), 5.95 (dd, IH, J=3.2, 10.1 Hz H-3), 5.74-5.62 (m, 2H), 5.49-5.48 (m, 1H), 4.54-4.43 (m, 1H, H-5), 4.21 (d, 1H, J=4.0 Hz; —OH), 1.37 (d, 3H J=6.2 Hz —$CH_3$).

$^{13}$C NMR (62.9 MHz $CDCl_3$) is 166.0, 165.9, 165.8, 133.6, 133.5, 133.3, 130.0 (2), 129.9 (2), 129.8 (2), 129.4, 129.3, 129.2, 128.7 (2), 1285 (2), 128.4 (2), 92.3 (C-1, α), 72.1, 715, 69.9, 66.7, 17.8 (C-6);

An HRMS (FAB) calculated value for $C_{27}H_{24}NaO_8$($M^+$+Na) m/z is 488.1369, and an actual measured value is 499.1372.

Embodiment 3

Synthesis of 2,3,4-tri-O-benzoyl-L-rhamnono-1,5-lactone (VII)

PCC (30 g, 0.139 mmol) and well-dried 4 Å molecular sieves (25 g) are added into a flask under $N_2$ current. Dry $CH_2Cl_2$ (250 ml) is added to the flask and the flask is stirred for 1 hour at a room temperature and cooled to 0° C. The compound (VI) (16 g, 33.6 mmol) dissolved in dry $CH_2Cl_2$ (250 ml) is added to and stirred 4 hours at a room temperature. The reaction is finished with adding cool $Et_2O$ (200 ml) and filtered by silica gel. The solvent is vacuum concentrated, and then the compound (VU) (13.54 g, 85%) is isolated using flash column chromatography (toluene/EtOAc, 10:1, v/v).

VII; an amorphous white solid, Rf=0.51 (toluene/EtOAc, 10:1, v/v);

$[α]D^{22}$=–10.0 (c=0.5, $CHCl_3$);

IR(film) Vmax 3064, 3031, 2983, 2936, 1784, 1730, 1601, 1452, 1393, 1259, 1096, 1026 $cm^{-1}$;

$^1$H NMR (250 MHz; $CDCl_3$) δ 8.10-7.29 (m, 15H, aromatic H), 6.28 (d, 1H, J=3.8 Hz), 6.05 (dd, 1H, J=1, 4, 3.8 Hz), 5.34 (dd, 1H, J=1.4, 11.0 Hz), 4.96-4.85 (m, 1H, H-5), 1.61 (d, 3H, J=6.3 Hz —$CH_3$);

$^{13}$C NMR (62.9 MHz $CDCl_3$) δ 165.5 (C-1), 165.1, 164.9, 164.8, 134.0, 133.9, 133.8, 130.1 (4), 130.0 (2), 128.7 (5), 128.5 (3), 128.4, 74.8, 74.1, 71.8, 67.6, 19.0 (C-6);

An HRMS (FAB) calculated value for $O_{27}H_{23}O_8$ ($M^+$+H) m/z is 475.1393, and an actual measured value is 475.1393.

Embodiment 4

Synthesis of 2,4-di-O-benzoyl-3,6-dideoxy-L-erythro-hex-2-enono-1,5-lactone (VIII)

The compound (VII) (13.2 g, 27.8 mmol) is dissolved in $Et_3N$:$CHCl_3$ (1:4, 500 ml) under $N_2$ current and stirred for 16 hours at a room temperature. After the reaction is finished, it is washed by water. An organic layer is dried using anhydrous $MgSO_4$. The solution is vacuum concentrated and then the compound (VIII) (6.37 g, 65%) is isolated using flash column chromatography (toluene/EtOAc, 10:1, v/v).

VIII; a crystalline white solid, Rf=0.53 (toluene/EtOAe, 10:1, v/v);

mp 108-112° C. (lit.[40] mp 107-110° C.);

$[α]D^{21}$=–93.1 (c=1.0, $CHCl_3$) [lit.[43] $[α]D^{20}$=–93.0 (c=1.0, $CHCl_3$)];

IR(film) Vmax 3069, 3007, 2936, 2920, 1738, 1674, 1598, 1452, 1355, 1257, 1155, 1115, 1060 $cm^{-1}$;

$^1$H NMR (250 MHz $CDCl_3$) δ 8.13-7.44 (m, 10H, aromatic H), 6.71 (d, 1H, J=4.3 Hz H-3), 5.69 (t, 1R, J=4.7 Hz H-4), 5.00-4.90 (m, 1H, H-5), 1.64 (d, 3R, J=6.7 Hz —$CH_3$);

$^{13}$C NMR (62.9 MHz $CDCl_3$) δ 165.5, 164.3, 158.0 (C-2), 140.8, 134.3, 133.9, 130.5 (2), 130.0 (2), 128.7 (5), 127.9, 125.6, 77.4, 68.6, 18.4 (C-6);

An HRMS (FAB) calculated value for $C_{20}H_{17}O_6$ ($M^+$+H) m/z is 353.1025, and an actual measured value is 353.1023.

Embodiment 5

Synthesis of 2,4-di-O-bemoyl-3,6-dideoxy-L-arabino-hexono-1,5-lactone (IX)

The compound (VIII) (6.1 g, 17.31 mmol) is dissolved in EtOAc (300 ml) and then 10%-Pd/C (400 mg) is added and is stirred for 3 hours at a room temperature after being substituted with hydrogen gas. The reactant is filtered by using celite 545. The solution is vacuum concentrated and then the compound (IX) (5.2 g, 85%) is isolated using flash column chromatography (toluenelEtOAc, 10:1, v/v).

IX; a white solid, Rf=0.45 (toluenelEtOAc, 10:1, v/v);

$[α]D^{21}$=+18.4 (c=1.0, $CHCl_3$) [lit.[43] $[α]D^{20}$=+18.2 (c=1.0, $CHCl_3$)];

IR(film) Vmax 3031, 2982, 2939, 1724, 1601, 1452, 1383, 1273, 1114, 1070, 1028 $cm^{-1}$;

$^1$H NMR (250 MHz $CDCl_3$) δ 8.11-7.43 (m, 10H, aromatic H), 5.90 (dd, 1H, J=7.6, 12.0 Hz H-2), 5.30-5.25 (m, 1H, H-4), 4.87-4.77 (m, 1H, H-5), 2.78-2.52 (m, 2H, H-3 eq, 3ax), 1.58 (d, 3H, J=6.5 Hz —$CH_3$);

$^{13}$C NMR (62.9 MHz $CDCl_3$) δ 168.0 (C-1), 165.5 (2), 133.9, 133.8, 130.2 (2), 129.9 (2), 129.1, 129.0, 128.8 (2), 128.6 (2), 76.9, 70.5, 65.0, 30.2 (C-3), 19.3 (C-6);

An HRMS (FAB) calculated value for $C_{20}H_{19}O_6$ ($M^+$+H) m/z is 355.1182, and an actual measured value is 355.1178.

Embodiment 6

Synthesis of 2,4-di-O-benzoyl-3,6-dideoxy-L-arabino-hexopyranose (II)

(1) Preparation of 0.5M Diisoamylborohydride

1M $BH_3$-THF (65 ml) is cooled to $-10°$ C. under $N_2$ current, and then 2M 2,3-dimethyl-2-butene (65 ml) is gradually added. It is stirred for 2 hours at $0°$ C. and used in the reaction (2).

(2) Synthesis of 2,4-di-O-benzoyl-3,6-dideoxy-L-arabino-hexopyranose (n)

The compound (IX) (5 g, 14.11 mmol) dissolved in dry THF (15 ml) is added to 0.5M Diisoamylborohydride (127 ml) prepared in the reaction (1). Then, it is stirred for 20 hours at a room temperature. After the reaction is finished, water (3 ml) is added and then stirred for 30 minutes. The reaction mixture is cooled to $0°$ C., and then 30% $H_2O_2$ (15 ml) is added and 3N NaOH is added to maintain the pH 7-8. The solvent THF is vacuum concentrated, and then it is dissolved in $CH_2Cl_2$ (100 ml) and washed by water (50 ml). An organic layer is dried using anhydrous $MgSO_4$. The solution is vacuum concentrated, and then the compound (II) (4.72 g, 93.8%, α:β=4.6:1) is isolated using flash column chromatography (toluene/EtOAc, 10:1, v/v).

II α; a colorless syrup, Rf=0.23 (toluene/EtOAc, 10:1, v/v);
$[α]_D^{24}$=+51.4 (c=1.0, $CHCl_3$);
IR(film) Vmax 3448, 3065, 3027, 2979, 1720, 1601, 1452, 1270, 1112, 1095, 1068, 1025 $cm^{-1}$;
$^1$H NMR (250 MHz $CDCl_3$) δ 8.15-7.43 (m, 10H, aromatic H), 5.29 (s, 1H, H-1), 5.25-5.15 (m, 2H, H-2, H-4), 4.39-4.28 (m, 1H, H-5), 3.51 (d, 1H, J=3.6 Hz —OH), 2.44 (td, 1H, J=3.8, 13.5 Hz H-3 eq), 2.29 (ddd, 1H, J=3.1, 11.0, 13.7 Hz H-3ax), 1.30 (d, 3H, J=6.2 Hz —$CH_3$);
$^{13}$C NMR (62.9 MHz $CDC_3$) δ 166.0, 165.8, 133.5, 133.4, 130.0 (3), 129.8 (3), 128.6 (4), 91.1 (C-1, α), 71.0 (C-2), 70.7 (C-4), 67.0 (C-5), 29.2 (C-3), 18.0 (C-6);
An HRMS (FAB) calculated value for $C_{20}H_{21}O_6$ ($M^+$+H) m/z is 357.1338, and an actual measured value is 357.1334.

Embodiment 7

Synthesis of (2R)-7-Octene-2-ol (III)

(1) Synthesis of 4-pentenylmagnesium bromide 5-bromo-1-pentene (2.8 ml, 23.5 mmol) dissolved in dry THF (20 ml) is added to Mg suspension (571 mg, 23.5 mmol) dissolved in dry THF (3 ml) dropwise for over 30 minutes. The reaction mixture is refluxed for 3 hours at $60°$ C., after which it is cooled to a room temperature, thereby preparing Grignard solution.

(2) Synthesis of (2R)-7-Octene-2-ol (III)

(R)-(+)-1,2-epoxypropane (1.12 ml, 16.0 mmol) is dissolved in dry THF (23 ml) and CuBr (230 mg, 1.6 mmol) is added therein, after which the temperature is reduced $-78°$ C. The 1M 4-pentenylmagnesium bromide solution (23 ml, 23.5 mmol) prepared in the reaction (1) is added to reaction mixture. The temperature is gradually increased to a room temperature and the mixture is stirred for 4 hours. The reaction is finished with saturated $NH_4Cl$ solution (10 ml). An obtained product is extracted with $Et_2O$ (20 ml×2) and it is washed by water (10 ml). An organic layer is dried using anhydrous $MgSO_4$. The solution is vacuum concentrated, and then the compound (III) (1.3 g, 65%) is isolated using flash column chromatography ($Et_2O$/n-pentene, 5:1, v/v):

III; a colorless liquid, Rf=0.15 ($Et_2O$/n-pentene, 5:1, v/v);
$[α]_D^{23}$=−10.7 (c=0.28, $CHCl_3$);
IR(film) Vmax 3357, 2969, 2930, 2858, 1641, 1460, 1416, 1374, 1305, 1122 $cm^{-1}$;
$^1$H NMR (250 MHz $CDCl_3$) δ 5.89-5.73 (m, 1H, H-2), 5.03-4.92 (m, 2H, H-1), 3.80-3.78 (m, 1H, H-7), 2.07 (m, 2H, H-3), 1.43-1.39 (m, 6H, H-4, 5, 6), 1.18 (d, 3H, J=6.1 Hz —$CH_3$);
$^{13}$C NMR (62.9 MHz; $CDCl_3$) δ 138.9 (C-2), 114.4 (C-1), 68.0 (C-7), 39.2 (C-6), 33.8 (C-3), 29.0 (C-4), 25.3 (C-5), 23.5 (C-8)

Embodiment 8

Synthesis of (2R)-Oct-7-en-2-yl-2,4-di-O-benzyl-3,6-dideoxy-α-L-arabino-hexopyranoside (X)

The compound (II) (2.0 g, 5.61 mmol, 1 eq), the compound (III) (1/08 g, 8.42 mmol), and 4 Å molecular sieves (200 g) are dissolved in dry $CH_2Cl_2$ (30 ml) under $N_2$ current, after which the temperature is cooled to $0°$ C. $BF_3$-$Et_2O$ (2.85 ml, 16.8 mmol, 4 eq) is gradually added and stirred for 10 hours, after which $Et_3N$ (5 ml) is added, and the reaction is finished and filtered. The solution is vacuum concentrated, and then the compound (X) (1.89 g, 72%) is isolated using flash column chromatography (n-hexane/EtOAc, 5:1, v/v).

VII; a colorless syrup, Rf=0.55 (n-hexane/EtOAc, 5:1, v/v);
$[α]_D^{22}$=+0.9 (c=1.0, $CHCl_3$);
IR(film) Vmax 3069, 2974, 2933, 2859, 1723, 1602, 1451, 1316, 1267, 1152, 1108, 1068, 1025 $cm^{-1}$;
$^1$H NMR (250 MHz $CDCl_3$) δ 8.14-7.42 (m, 10H, aromatic H), 5.93-5.76 (m, 1H), 5.26-5.16 (m, 2H, H-2, H-4), 5.07-5.00 (m, 3H, H-1), 4.20-4.09 (m, 1H, H-5), 3.85 (m, 1H), 2.48-2.41 (m, 1H, H-3'eq), 2.28-2.17 (m, 1H, H-3'ax), 2.11 (m, 2H), 1.68-1.37 (m, 6H), 1.30 (d, 3H, J"=6.2 Hz), 1.20 (d, 3H, 6.1 Hz);
$^{13}$C NMR (62.9 MHz; $CDCl_3$) δ 165.9, 165.7, 138.9, 133.3, 133.2, 129.9 (3), 129.6 (2), 128.5 (4), 114.5, 93.8 (C-1', α), 72.5, 71.3, 70.7, 67.0, 37.0, 33.8, 29.8, 28.8, 25.3, 19.2, 17.9;
An HRMS (FAB) calculated value for $C_{28}H_{35}O_6$ ($M^+$+H) m/z is 467.2434, and an actual measured value is 467.2438.

Embodiment 9

Synthesis of (6R)-6-(2,4-di-O-benzoyl-3,6-dideoxy-α-L-arabino-hexopyranosyl) heptanoic acid (XI)

The compound (X) (1.8 g, 3.86 mmol) is dissolved in acetone and then $NaHCO_3$ (972 mg, 11.57 mmol) is added to therein. Then, $KNnO_4$ (3 g, 19.29 mmol) is gradually added and it is stirred for 12 hours. After the reaction is finished, it is acidified using 10% HCl (20 ml). An obtained product is extracted with EtOAc (100 ml×2) and is washed by brine (70 ml). An organic layer is dried by anhydrous $MgSO_4$. The solution is vacuum concentrated, and then the compound (XI) (1.51 g, 87%) is isolated using flash column chromatography (n-hexane/EtOAc, 5:1, v/v).

XI; a colorless syrup, Rf=0.13 (hexane/EtOAc, 5:1, v/v);
$[α]_D^{22}$=−1.9 (c=1.0, $CHCl_3$);

IR(film) Vmax 3063, 2973, 2935, 1721, 1602, 1451, 1316, 1267, 1109, 1068, 1025 cm$^{-1}$;

$^1$H NMR (250 MHz; CDCl$_3$) δ 10.69 (bs, 1H, —OH), 8.14-7.42 (m, 10H, aromatic H), 5.26-5.17 (m, 2H, H-2' H-4'), 4.98 (s, 1H, H-1'), 4.19-4.08 (m, 1H, H-5'), 3.87 (m, 1H), 2.47-2.36 (m, 3H), 2.28-2.17 (m, 1H, H-3'ax). 1.72-1.45 (m, 6H), 1.31 (d, 3H, J=6.2 Hz), 1.21 (d, 3R, J=6.0 Hz);

$_{13}$C NMR (62.9 MHz CDCl$_3$) δ 179.8, 165.8, 165.7, 133.3, 133.2, 130.0, 129.9 (2), 129.8, 129.7 (2), 128.5 (4), 93.8 (C-1', α), 72.4, 71.2, 70.7, 67.1, 36.7, 34.0, 29.7, 25.2, 24.6, 19.1, 17.9;

An HRMS (FAB) calculated value for C$_{27}$H$_{33}$O$_8$ (M$^+$+H) m/z is 485.2175, and an actual measured value is 485.2165.

Embodiment 10

Synthesis of 6R-(3,6-dideoxy-L-arabino-hexopyranosyloxy)heptanoic acid (I)

The compound (XI) (472.9 mg, 0.976 mmol) is dissolved in MeOH (20 ml) NaOMe (52.7 mg, 0.976 mmol) is added at 0° C. The temperature is gradually increased to a room temperature and the mixture is stirred for 12 hours. After the reaction is finished, MeOH is vacuum concentrated. Then, in order to eliminate a sub-product methylbenzoate, it is dissolved in water (20 ml) and washed by CH$_2$Cl$_2$ (20 ml×5). The pH of the solution layer is adjusted using amberlite resin type acid such as amberlite and amberlite IR-120 (H$^+$) (500 mg). After the filtration, the water is removed from the solution layer by freeze drying method, and then the compound (I) (234.6 mg, 87%) is isolated using flash column chromatography (EtOAc/MeOH, 11:1, v/v).

I; a colorless oil, Rf=0.43 (EtOAc/MeOH, 11:1, v/v);

[α]D$^{20}$=−81.0 (c=0.1, MeOH);

IR(film) Vmax 3391, 2969, 2933, 1712, 1452, 1379, 1244, 1126, 1103, 1042, 1031 cm$^{-1}$;

$^1$H NMR (500 MHz CD$_3$ OD) δ 4.64 (s, 1H, H-1'), 3.80-3.77 (m, 1H, H-6), 3.72-3.71 (m, 1H, H-2'), 3.63-3.59 (m, 1H, H-5'), 3.54-3.49 (m, 1H, H-4'), 2.30 (t, 2H, J=7.5 Hz; H-2), 1.96-1.92 (m, 1H, H-3' eq), 1.79-1.74 (m, 1H, H-3'ax), 1.61 (m, 2H, H-3), 1.56-1.50 (m, 2H, H-5), 1.47 (m, 2H, H-4), 1.21 (d, 3H, J=6.5 Hz H-6'), 1.12 (d, 3H, J=6.5 Hz H-7);

$^{13}$C NMR (125.7 MHz; CD$_3$OD) δ 177.7 (C-1), 97.6 (C-1', α), 72.4 (C-6), 71.3 (C-5'), 70.1 (C-2'), 68.5 (C-4'), 38.2 (C-5), 36.1 (C-3'), 35.0 (C-2), 26.5 (C-3), 26.1 (C-4), 19.4 (C-7), 18.2 (C-6');

An HRMS (FAB) calculated value for C$_{13}$H$_{25}$O$_6$ (M$_+$+H) m/z is 277.1651, and an actual measured value is 277.1652.

Embodiment 11

Synthesis of base addition salts (I-1: n=4, X=Na) of 6R-(3,6-dideoxy-L-arabino-hexopyranosyloxy)heptanoic acid (I)

The compound (I) (267 mg, 1.0 mmol) is dissolved in MeOH (10 ml). NaOMe (40.0 mg, 1.0 mmol) is added at 0° C. Then, the temperature is gradually increased to a room temperature and the mixture is stirred for 1 hour. After the reaction is finished, MeOH is vacuum concentrated and filtered. Then, the water is removed from a solution layer by freeze drying method, and the compound (I-1) (271 mg, 95%) is isolated.

Test Example

Measurement of Dauer Formation Effect Activity

To identify the dauer formation effect of the inventive pheromone, an activity is measured after the pheromone compound is supplied to S. basal agar culture medium without peptone (Vowels and Thomas, Genetics 130: 105-123, 1992).

The dauer formation effect activity of the inventive compound with respect to *C. elegance* is shown as Table 3.

TABLE 4

(Spectrum analysis result of pheromone, 6R-(3,6-dideoxy-L- arabino-hexopyranosyloxy) heptanoic acid

| Position | δ$_H$ (mult, J ) | δ$_C$ | HMBC (H to C) |
|---|---|---|---|
| 1 | | 177.3 | 2, 3 |
| 2 | 2.30 (t, 7.5) | 34.6 | 1, 3 |
| 3 | 1.64 (m) | 25.5 | 2, 4, 5, 6 |
| 4 | 1.47 (m) | 25.1 | 2, 3, 5 |
| 5 | 1.50-1.48 (m) | 37.1 | 3, 4, 6, 7 |
| 6 | 3.80-3.77 (m) | 71.3 | 5, 7, 1' |
| 7 | 1.14 (d, 6.5) | 18.3 | 5, 6 |
| 1' | 4.66 (s) | 96.6 | 2', 3', 6 |
| 2' | 3.73-3.72 (m) | 69.0 | 1', 3' |
| 3' | 1.97-1.95 (m) 1.79-1.74 (m) | 34.9 | 1', 4', 5' |
| 4' | 3.54-3.59 (m) | 67.4 | 3', 5', 6' |
| 5' | 3.64-3.62 (m) | 70.2 | 3', 4', 6' |
| 6' | 1.24 (d, 6.5) | 17.2 | 4', 5' |

INDUSTRIAL APPLICABILITY

As described above, the present invention firstly determined stereochemistry configuration of pheromone, (6R)-6-(3.6-dideoxy-L-arabino-hexopyranosyloxy) heptanoic acid and salts thereof. Based on this fact, the effective total synthesis was successfully performed, thereby overcoming the minute isolation of the pheromone obtained from *C. elegance* to make it possible to mass-produce the pheromone.

Accordingly, it becomes possible to develop medical substances using the pheromone relating to aging, stress, metabolism, signal transfer system in vivo, and anti-cancer, obesity and a suppressing agent for aging and stress. In addition, it becomes also possible to research the active target protein body of the pheromone.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A process for preparing pheromone compound having a stereochemistry formula (I-1) wherein in formula I-1 n=4 and X=H, the method comprising the steps of:
   acetalating a compound of formula (II) with compound of formula (III) in the presence of Lewis acid catalyst;
   converting the aliphatic terminal double bond of the produced coupling reactant to an organic acid by an oxidant; and
   removing the two O-benzoyl protecting groups of the 3-deoxyrhamnosyl group with a base and acidifying with an acid

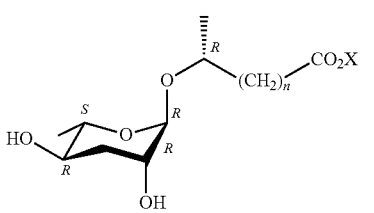
(I-1)

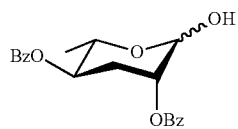
(II)

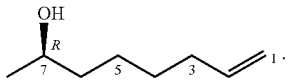
(III)

2. The process of claim 1, wherein the catalyst is $BF_3$-$Et_2O$ and molecular sieves.

3. The process of claim 1, wherein the oxidant is $KMnO_4$ and $NaHCO_3$ is used as a supplement agent.

4. The process of claim 1, wherein the base is NaOH or KOH and the acid is amberlite.

5. The process of claim 1, wherein the compound of formula (II) is obtained from compound of formula (VII)

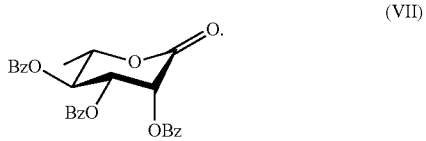
(VII)

6. The process of claim 5, wherein the compound of formula (VII) is obtained by oxidizing the compound of formula (VI)

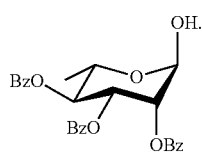
(VI)

* * * * *